United States Patent [19]

Lantzsch

[11] Patent Number: 4,602,117

[45] Date of Patent: Jul. 22, 1986

[54] PROCESS FOR THE PREPARATION OF HALOGENATED 3,3-DIMETHYL-5-HEXEN-2-ONES

[75] Inventor: Reinhard Lantzsch, Wuppertal, Fed. Rep. of Germany

[73] Assignee: Bayer Aktiengesellschaft, Leverkusen, Fed. Rep. of Germany

[21] Appl. No.: 795,683

[22] Filed: Nov. 6, 1985

[30] Foreign Application Priority Data

Nov. 13, 1984 [DE] Fed. Rep. of Germany ....... 3441370

[51] Int. Cl.⁴ .............................................. C07C 45/70
[52] U.S. Cl. ..................................... 568/393; 568/388
[58] Field of Search ........................ 568/393, 391, 388

[56] References Cited

U.S. PATENT DOCUMENTS 2,482,066  9/1949  Hull et al. ............................ 568/388
3,337,634  8/1967  Thompson ............................ 568/391
3,655,768  4/1972  Pommer et al. ....................... 568/391

OTHER PUBLICATIONS

Seyfarth, Chem. Abst., vol. 69, #26709n (1968).
Mitzner et al., Chem. Abst., vol. 99, #157524r (1983).
Takagi et al., Chem. Abst., vol. 57, #4850G (1962).
Soulen et al., J. Org. Chem. vol. 36, #22, pp. 3386–3391, (1971).

*Primary Examiner*—James H. Reamer
*Attorney, Agent, or Firm*—Sprung Horn Kramer & Woods

[57] ABSTRACT

A process for the preparation of halogenated 3,3-dimethyl-5-hexen-2-ones of the formula

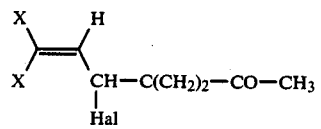

wherein an acetic acid ester of the formula

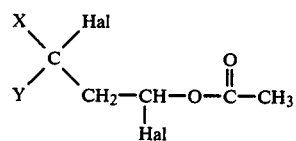

is reacted with 2-methylbutan-3-one of the formula

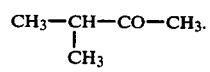

8 Claims, No Drawings

PROCESS FOR THE PREPARATION OF HALOGENATED 3,3-DIMETHYL-5-HEXEN-2-ONES

The present invention relates to a new process for the preparation of halogenated 3,3-dimethyl-5-hexen-2-ones.

It is already known that halogenated 3,3-dimethyl-5-hexen-2-ones can be prepared, for example, by reacting vinyl aldehydes with 2-methylbutan-3-one in the presence of hydrogen halide acids. These syntheses are expensive, because the vinyl aldehydes are difficult to obtain. Further disadvantages in the use of vinyl aldehydes are their sensitivity to hydrolysis and their instability. On an industrial scale, the vinyl aldehydes can only be handled with difficulty and can only be obtained in satisfactory yields from vinyl butyl ether, which is expensive (see J. Org. Chem. 36, 3390 (1971) and EP-OS (European Published Specification) 31,041).

It has now been found that halogenated 3,3-dimethyl-5-hexen-2-ones of the formula (I)

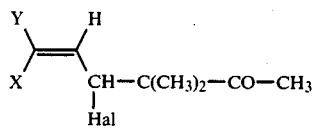

in which
X represents halogen,
Y represents halogen or trihalogenoalkyl and
Hal represents chlorine or bromine are obtained by reacting acetic acid esters of the formula (II)

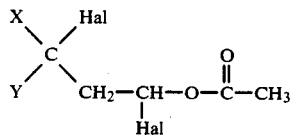

in which
X, Y and Hal have the meanings indicated above with 2-methylbutan-3-one of the formula (III)

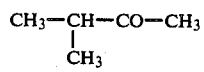

in the presence of aqueous hydrogen halide acids and, if appropriate, in the presence of additional inert diluents.

Surprisingly, the compounds of the general formula (I) can be prepared in a simple manner in smooth reactions, excellent yields being obtained. Because the individual intermediate products are stable and, above all, can be stored for a prolonged period if they are isolated, the process according to the invention also permits an exceptional flexibility in production, so that, if demand for the end products increases rapidly, manufacture is possible in step with demand, which can be of very great importance, in particular, as a result of the considerable, climate-induced seasonal variations in the plant protection sector.

Surprisingly, the acetic ester compound of the formula (II) can be reacted with 2-methylbutan-3-one of the formula (III) in a higher yield than the corresponding vinyl aldehydes. The reaction according to the invention does not pass through the aldehyde stage.

If, for example, 1,3,3,3-tetrachloropropyl acetate and 2-methylbutan-3-one are used as the starting materials, the progress of the reaction can be reproduced by the following equation:

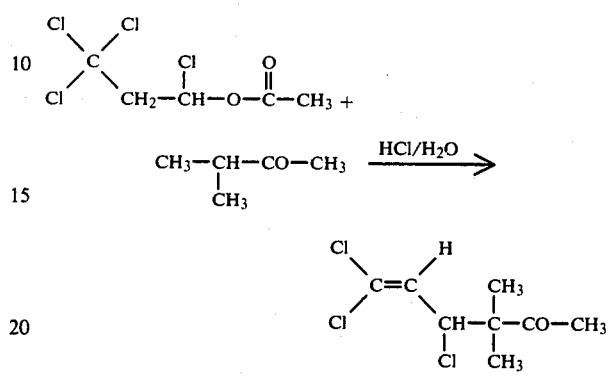

The acetic acid esters to be used in the process according to the invention are defined in a general manner by the formula (II). In this formula
X preferably represents fluorine, chlorine or bromine,
Y preferably represents fluorine, chlorine, bromine or halogeno-$C_1$-$C_4$-alkyl and
Hal preferably represents chlorine or bromine.

Compounds of the formula (II) which are particularly preferred are those in which
X represents fluorine, chlorine or bromine,
Y represents fluorine, chlorine, bromine or trifluoromethyl and
Hal represents chlorine or bromine.

The compounds of the formula (II) are known and/or can be prepared by known methods, for example by reacting the compounds of the formula (IV)

in which
X, Y and Hal have the meanings indicated above, with vinyl acetate of the formula (V)

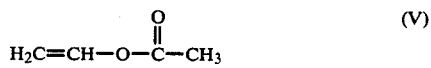

in the presence of catalysts which are customarily used for the addition reactions of such compounds with the olefines, such as, for example, peroxides or other free radical-formers, such as, for example azobisisobutyronitrile, or copper-(I) chloride or redox catalysts, in the presence of inert diluents, such as, for example, acetonitrile, and at temperatures between 40° C. and 130° C. (see J. Chem. Soc. 1963, 1887 and the example of preparation).

The following, for example, may be mentioned as examples of the compounds of the formula (II): 1,3,3,3-tetrachloropropyl acetate, 1-bromo-3,3,3-trichloropropyl acetate, 1,3,3,3-tetrabromopropyl acetate and 1,3-dibromo-3,3-difluoropropyl acetate and also 1,3,3-trichloro-4,4,4-trifluorobutyl acetate.

The compounds of the formula (III), (IV) and (V) are known compounds of organic chemistry.

The reaction can be carried out with or without additional diluents. Suitable diluents are any diluents which are inert towards hydrochloric or hydrobromic acid, such as, for example, hydrocarbons, such as cyclohexane, petroleum ether, benzene or toluene, or chlorinated hydrocarbons, such as methylene chloride, chloroform, carbon tetrachloride or chlorobenzene; ethers, such as diethyl ether, diisopropylether, tetrahydrofuran, dioxane or 1,2-dimethoxyethane, and acids, such as acetic acid.

If solvents which are virtually immiscible with water are used, it is preferable to employ phase transfer catalysts belonging to the series of tetraalkylammonium or trialkylaralkylammonium salts, such as, for example, tetrabutylammonium bromide or triethylbenzylammonium chloride.

It is preferable to carry out the reaction without additional diluents.

The process according to the invention is carried out in the presence of excess hydrochloric or hydrobromic acid.

The reaction temperatures can be varied within a fairly wide range, but, surprisingly, the reaction takes place even under extremely mild conditions. In general, the reaction is carried out between 0° C. and 100° C., but preferably between 30° C. and 80° C.

In carrying out the process according to the invention, the starting materials (II) and (III) are usually employed in equimolar amounts. An excess of 2-methylbutane-3-one of the formula (III) is, however also possible. In general, when the process according to the invention is carried out, it is preferable to add the hydrogen halide acid to a mixture of (II) and (III). In principle, however, it is also possible to proceed in the converse order. The isolation of the compounds, according to the invention, of the formula (I) is effected in accordance with customary methods of extraction and distillation.

The compounds of the formula (I) are important intermediate products for the preparation of 3-vinyl-2,2-dimethylcyclopropanecarboxylic acids or esters thereof, which are compounds having a high insecticidal potency (see, for example, DE-OS (German Published Specifications) Nos. 2,706,184 and 2,738,150).

The compounds of the formula (I) can, for example, be reacted as follows to give 3-vinyl-2,2-dimethylcyclopropanecarboxylic acids or esters thereof:

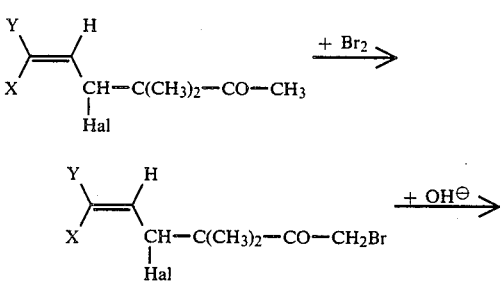

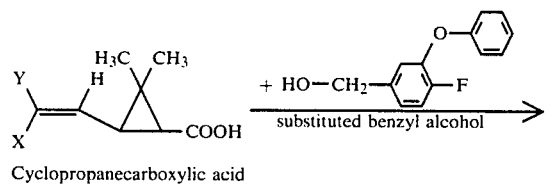

Cyclopropanecarboxylic acid

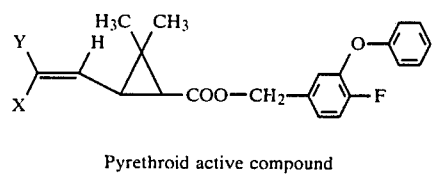

Pyrethroid active compound

EXAMPLE 1

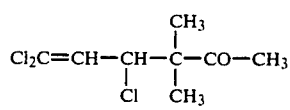

A mixture of 24 g (0.1 mole) of 1,3,3,3-tetrachloropropyl acetate and 9.5 g (0.11 mole) of methyl isopropyl ketone is heated to 55° C. with stirring, and 100 ml of concentrated hydrochloric acid are added dropwise. The mixture is stirred at 55° C. for 12 hours, cooled and diluted with water. The reaction solution is extracted three times with methylene chloride, and the organic phase is washed with water, dried and concentrated. The ketone can be purified by distillation in a high vacuum.

21.1 g (91.9%) of theory) of 4,6,6-trichloro-3,3-dimethyl-5-hexen-2-one of boiling point 85° C./0.1 mbar are obtained in the form of a yellow oil.

EXAMPLE 2

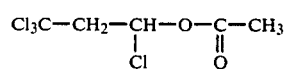

740 g of carbon tetrachloride are heated to 75° to 80° C. with stirring. A mixture of 207 g of vinyl acetate and 2 g of azobisisobutyronitrile in 275 g of carbon tetrachloride is then added dropwise in the course of 20 hours, and the mixture is stirred for a further 2 hours. After it has cooled to 20° C., it is washed with 10% strength aqueous sodium bicarbonate solution and dried over sodium sulphate. Carbon tetrachloride is removed by distillation, and the residue is fractionated in a high vacuum.

160 g (24.5% of theory) of 1,3,3,3-tetrachloropropyl acetate of boiling point 64°–65° C./2 mbar are obtained.

We claim:

1. Process for the preparation of a halogenated 3,3-dimethyl-5-hexen-2-ones of the formula (I)

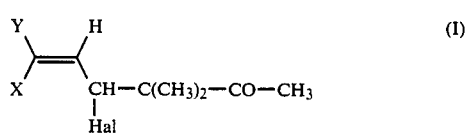

in which

X represents halogen,

Y represents halogen or trihalogenoalkyl and
Hal represents chlorine or bromine, wherein an acetic acid ester of the formula (II)

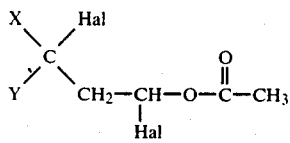 (II)

in which

X, Y and Hal have the meanings indicated above is reacted with 2-methylbutan-3-one of the formula (III)

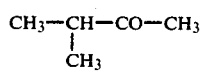 (III)

in the presence of an aqueous hydrogen halide acid and, if appropriate, in the presence of an additional inert diluent.

2. Process according to claim 1 for the preparation of a compound of the formula (I) in which
X represents fluorine, chlorine or bromine,
Y represents fluorine, chlorine, bromine or halogeno-$C_1$-$C_4$-alkyl and
Hal represents chlorine or bromine.

3. Process according to claim 1 for the preparation of a compound of the formula (I) in which
X represents fluorine, chlorine or bromine,
Y represents fluorine, chlorine, bromine or trifluoromethyl and
Hal represents chlorine or bromine.

4. Process according to claim 1, wherein the reaction is carried out without additional inert solvents.

5. Process according to claim 1, wherein the reaction is carried out in the presence of excess hydrochloric or hydrobromic acids.

6. Process according to claim 1, wherein the reaction is carried out between 0° C. and 100° C.

7. Process according to claim 1, wherein the reaction is carried out between 30° C. and 80° C.

8. Process according to claim 1, wherein the acetic acid ester and 2-methylbutan-3-one are employed in equimolar amounts.

* * * * *